United States Patent
Dahlberg et al.

(10) Patent No.: US 11,319,572 B2
(45) Date of Patent: May 3, 2022

(54) APPARATUS AND METHOD FOR CARRYING OUT AN INTEGRITY TEST

(71) Applicant: Sartorius Stedim Biotech GmbH, Goettingen (DE)

(72) Inventors: Martin Dahlberg, Bovenden (DE); Isabelle Gay, Peypin (FR); Marie Christine Menier, La Ciotat (FR); Nelly Montenay, Rousset (FR)

(73) Assignee: Sartorius Stedim Biotech GmbH

( * ) Notice: Subject to any disclaimer, the term of this patent is extended or adjusted under 35 U.S.C. 154(b) by 588 days.

(21) Appl. No.: 15/316,597

(22) PCT Filed: Jul. 8, 2015

(86) PCT No.: PCT/EP2015/001390
§ 371 (c)(1),
(2) Date: Dec. 6, 2016

(87) PCT Pub. No.: WO2016/008574
PCT Pub. Date: Jan. 21, 2016

(65) Prior Publication Data
US 2018/0148759 A1     May 31, 2018

(30) Foreign Application Priority Data

Jul. 17, 2014  (DE) .................. 10 2014 010 559.8
Jan. 9, 2015   (DE) .................. 10 2015 000 314.3

(51) Int. Cl.
| | | |
|---|---|---|
| C12Q 1/04 | (2006.01) | |
| G01N 15/08 | (2006.01) | |
| G01N 17/00 | (2006.01) | |
| G01M 3/18 | (2006.01) | |

(Continued)

(52) U.S. Cl.
CPC .............. *C12Q 1/04* (2013.01); *G01M 3/186* (2013.01); *G01M 3/226* (2013.01); *G01M 3/26* (2013.01);
(Continued)

(58) Field of Classification Search
CPC .............. G01N 21/783; G01N 17/002; G01N 15/0826; G01N 15/0806; A61L 2/26;
(Continued)

(56) References Cited

U.S. PATENT DOCUMENTS

| | | | |
|---|---|---|---|
| 4,789,434 A | 12/1988 | Little et al. | |
| 4,791,805 A * | 12/1988 | Gates ................... | G01M 3/226 73/40.7 |
| 5,205,157 A * | 4/1993 | McDaniel .......... | G01M 3/3281 73/49.2 |
| 5,681,740 A * | 10/1997 | Messier ................... | A01N 1/02 206/438 |

(Continued)

FOREIGN PATENT DOCUMENTS

| | | |
|---|---|---|
| CN | 1890546 A | 1/2007 |
| CN | 102989324 A | 3/2013 |

(Continued)

OTHER PUBLICATIONS

International Search Report dated Nov. 4, 2015.

*Primary Examiner* — Jill A Warden
*Assistant Examiner* — John McGuirk
(74) *Attorney, Agent, or Firm* — Gerald E. Hespos; Michael J. Porco; Matthew T. Hespos (57) ABSTRACT

A device (1; 2; 3; 4; 5) is provided for carrying out an integrity test on a sample of disposable components. The device has a medium chamber (10) with an inner chamber (11) that is bounded to the outside, for the purpose of receiving a culture medium. The device also has a sample holder (20) in which the sample (100) can be arranged in (Continued)

such a way that the sample (100) at least partially bounds the medium chamber (10) to the outside. The medium chamber (10) has a vent line (19) that is arranged on a side of the medium chamber (10) facing away from the sample holder (20).

9 Claims, 6 Drawing Sheets

(51) Int. Cl.
  *G01M 3/22* (2006.01)
  *G01M 3/32* (2006.01)
  *G01M 3/26* (2006.01)
(52) U.S. Cl.
  CPC ...... *G01M 3/3272* (2013.01); *G01N 15/0806* (2013.01); *G01N 15/0826* (2013.01); *G01N 17/002* (2013.01)
(58) Field of Classification Search
  CPC .......... A61L 2202/181; B65D 81/2061; B65D 81/2084; B65D 79/02; B65D 75/38; A61J 1/14; C12Q 1/04; G01M 3/3272; G01M 3/226; G01M 3/186; G01M 3/26
  USPC ...... 436/1, 3; 206/569, 534, 438, 459.1, 807
  See application file for complete search history.

(56) References Cited

U.S. PATENT DOCUMENTS

| | | | |
|---|---|---|---|
| 7,555,934 B2 * | 7/2009 | DeRoos | G01N 15/0826 73/38 |
| 2004/0129060 A1 | 7/2004 | Grummert et al. | |
| 2006/0121613 A1 | 6/2006 | Havens | |
| 2007/0220956 A1 * | 9/2007 | Terentiev | G01M 3/187 73/49.2 |
| 2009/0320564 A1 * | 12/2009 | Piombini | G01N 15/0826 73/38 |
| 2011/0265820 A1 | 11/2011 | Dahlberg et al. | |
| 2013/0055792 A1 | 3/2013 | Scheu et al. | |
| 2014/0060159 A1 * | 3/2014 | Sharma | G01N 15/0806 73/38 |
| 2016/0263263 A1 * | 9/2016 | Robert | A61L 2/14 |

FOREIGN PATENT DOCUMENTS

| | | |
|---|---|---|
| DE | 101 16 335 | 10/2002 |
| DE | 10 2004 016 592 | 10/2005 |
| DE | 10 2010 018 881 | 11/2011 |
| FR | 2 960 972 | 12/2011 |
| WO | 2008/030712 | 3/2008 |

\* cited by examiner

APPARATUS AND METHOD FOR CARRYING OUT AN INTEGRITY TEST

BACKGROUND

1. Field of the Invention.

The invention relates to a device and a method for carrying out an integrity test on a sample of disposable components, and to the use of such an apparatus.

2. Description of the Related Art.

In the biopharmaceutical industry, a move is being made away from stainless steel components toward disposable components. Since disposable plastic components can be damaged more easily during production, transport and handling than equipment made of stainless steel components, an integrity test of the disposable components is often demanded by customers and regulatory authorities. This integrity test can be a leakage test in which the disposable component is tested for a leak, and in which the disposable component is not destroyed. Alternatively or additionally, a verification of the functionality of the disposable component as a sterile barrier can be carried out as the integrity test—for example a bacterial retention test (abbreviated BCT, "Bacteria Challenge Test") in which the disposable component is destroyed.

Common bacteria challenge tests by immersion in accordance with ISO 15747 and by aerosol are often limited in their implementation in size—for example by restricted spatial expansion of an aerosol chamber used for this purpose. Other difficulties in carrying out a BCT are found in the handling of samples of the disposable components when the integrity test is carried out, without cross-contamination by the experimenter.

A cleaning method for an inspection device is known from DE 10 2010 018 881 A1, wherein the selected internal volumes are cleaned with a cleaning fluid and rinsed with a rinsing fluid. In this case, a retaining device can have an upstream vent.

A method for carrying out an integrity test of filter elements is known from DE 101 16 335 C1, wherein a convective component of a gas volumetric flow rate is determined by the filter elements from a ratio of gas volumetric flow rates and a ratio of solubility and/or diffusion coefficients in a wetting liquid of the filter elements of two different test gases. A test device can be used which can accommodate test gases.

The problem addressed by the invention is that of enabling an improved and/or simplified integrity test of samples of disposable components.

SUMMARY

A first aspect relates to a device for carrying out an integrity test on a sample of disposable components, having a medium chamber with an inner chamber which is bounded to the outside, for the purpose of receiving a culture medium, and having a sample holder in which the sample can be arranged in such a way that the sample at least partially bounds the medium chamber to the outside. The medium chamber in this case has a vent line which is arranged on the side of the medium chamber which faces away from the sample holder.

In this case, a punched-out piece of film or foil of the disposable component, with or without a weld, can be used as a sample of a disposable component. Additional components can be welded into the samples—for example, fluid ports with or without additional tubing. The samples are substantially flat and have an inner sample surface and an opposing outer sample surface. If such a sample is placed in the sample holder, the inner sample surface faces the inner chamber of the medium chamber, while the outer sample surface faces outward and can be exposed to bacteria and/or spores. In particular, the samples can be disk-shaped, for example with a diameter of about 50 mm. When samples of this size are used, the device can itself have a limited radial expansion, for example of maximum 100 mm in diameter.

The integrity test can contain in particular a BCT—that is, a bacteria challenge test—in which the medium chamber is investigated for contamination which passes through the sample. The integrity test can be further correlated with a leak test.

To perform the integrity tests, the medium chamber is filled with a culture medium, such as with TSB (tryptic soy broth). The medium chamber in this case is designed to be leak-free to such an extent that it can hold a culture medium which is, by way of example, liquid, substantially without notable volatilization, over several days. The inner chamber of the medium chamber can be designed in particular to be impermeable to the medium and/or liquid.

The sample of a disposable component can be placed in the sample holder in such a manner that the sample closes off the medium chamber in a medium-tight manner. For this purpose, the sample holder can at least partially bound the medium chamber to one side thereof. The sample is placed—for example, clamped into—the sample holder. The sample holder can have sealing elements, for example in the form of O-rings, which enable a media-tight arrangement of the sample in the sample holder. The sample arranged in the sample holder provides a boundary surface of the medium chamber.

The vent line is designed and included to vent the medium chamber of gases therein, in particular air. The vent line provides a venting option on the side of the medium chamber which faces away from the sample holder and thus the sample. The vent line can be designed, for example, on a lateral wall of the medium chamber which is opposite the medium chamber. Thus, the sample holder and the sample can be disposed in a first side of the medium chamber. The vent line is connected in this embodiment on a second side of the medium chamber which is remote from the first side of the medium chamber and is optionally located opposite the same.

An opening is formed for this purpose in the side of the medium chamber which faces away from the sample holder, the vent line connecting to the same, and the inner chamber of the medium chamber able to be vented by the same. In one embodiment, the vent line is configured as a closable valve. In another embodiment, the vent line is configured as a closable tubular or hose-shaped conduit which is arranged running away from a vent opening in said side of the medium chamber.

The arrangement of the vent line on the side of the medium chamber opposite the sample holder enables a complete filling of the medium chamber with the culture medium. To this end, the medium chamber can be arranged so that the sample holder is arranged (with respect to the earth) at the bottom, while the vent line is arranged vertically above the sample holder. The indications "up", "down", "vertical" and "horizontal" make general reference in the context of the invention to the terrestrial reference system, and more specifically to the gravitational force in the terrestrial reference system. The medium chamber can be filled with a culture medium—which is, for example, liquid—via a separate medium line, said culture medium settling in the 
inner chamber of the medium chamber directly on the sample. Gas (such as air) in the medium chamber is lighter than the culture medium and therefore rises in the inner chamber of the medium chamber, i.e., in the direction of the side where the vent line is connected. When the vent line is open, the medium chamber can therefore be completely filled with the culture medium, while air in the inner chamber of the medium chamber can be fully discharged upward through the vent line.

The arrangement of the vent line opposite the sample thus allows for a direct application of the culture medium to the sample, in particular the inner sample surface, on the one hand, and on the other hand allows a complete filling of the medium chamber with the culture medium.

According to one embodiment, the device comprises an alignment device, by means of which the medium chamber can be aligned in a filling position in which the medium chamber can be filled with the culture medium and in which the sample holder is arranged vertically below the vent line. The alignment device can be designed for example as a pivot device with a substantially horizontally aligned pivot axis. The medium chamber is pivotable about the pivot axis, so that the sample holder is arranged on the lower end of the medium chamber, and the vent line is arranged on the upper end of the medium chamber. The alignment device in particular enables a positioning of the point of engagement of the vent line with the medium chamber substantially at the uppermost and/or the highest point of the medium chamber, such that gas bubbles which are present, for example, at atmospheric pressure can escape from the medium chamber, wherein the same could otherwise act as a buffer for the medium at a defect point of the sample. The medium chamber can thus be completely filled when filled with a culture medium. Furthermore, the alignment device can be designed as a mounting of the medium chamber.

In one implementation of this embodiment, the medium chamber can also be aligned by means of the alignment device in a suspension filling position in which the sample holder is positioned vertically above the vent line. In the suspension filling position, the sample at least partially provides an upper lateral wall of the medium chamber. In the suspension filling position, an optionally present suspension chamber can be filled in a particularly favorable manner with a suspension, as described further below.

Alternatively or additionally, the medium chamber is aligned by means of the alignment device in an application position. In the application position, an aerosol or a suspension containing the bacteria and/or spores can be applied in a particularly favorable manner to the sample. In the application position, the outer sample surface can be substantially oriented horizontally and facing upwards. Alternatively, in the application position the outer sample surface is inclined to the horizontal. In the latter case, the sample can be arranged with its outer sample surface substantially vertically or with an inclination to the horizontal—that is, at an angle of 10° to 90°, in particular 40° to 90° with respect to the horizontal.

Upon application of an aerosol to the medium chamber in the suspension filling position, the aerosol can fall and/or be deposited on the sample. If a suspension is applied in the suspension filling position, the gravitational force of the suspension acts directly on the sample arranged on the upper side of the medium chamber.

The suspension filling position is provided for filling the suspension chamber, and is distinguished from the filling position, which is provided for the filling of the medium chamber, by the orientation of the device.

In the filling position, the vent line of the medium chamber can be arranged at the vertically highest point of the medium chamber, and the sample holder on the vertically lowest point of the medium chamber. In this arrangement, the medium chamber can be particularly well vented, and the sample is particularly effectively and extensively covered by the culture medium.

According to one embodiment, the device comprises a connecting element to connect the medium chamber to a suspension chamber, in such a manner that the sample arranged in the sample holder provides a boundary surface between the inner chamber of the medium chamber and a suspension chamber inner chamber of the suspension chamber. The medium chamber can be separated in this case from the suspension chamber via only the sample arranged in the sample holder. The suspension chamber can have a medium-tight design and be used for receiving a suspension which contains the bacteria and/or spores. The suspension chamber can be arranged via the connecting element on the device in such a manner that the suspension chamber is arranged on the outer sample surface—i.e., the side of the sample which is remote from the medium chamber. The sample can be arranged as a boundary surface between the medium chamber and the suspension chamber. If a bacteria and/or spore suspension is arranged in the suspension chamber, the suspension is applied directly to the sample. As a result, the integrity test can determine whether the sample is permeable to the bacteria and/or spores in the suspension. If the sample is permeable, then a growth can be observed in the culture medium which is arranged in the medium chamber. The connecting element can be designed, by way of example, as a threading, locking lug, and/or plug element. A corresponding counter connecting element can be arranged on the suspension chamber. The connecting element can in particular be constructed on the sample holder and serve the purpose of connecting the suspension chamber to the sample holder. In this case, the medium chamber can be connected via only the sample holder to the suspension chamber. The connection between the suspension chamber and the medium chamber can be detachable. For this purpose, both the connection of the medium chamber to the sample holder, and the connection of the suspension chamber to the sample holder, can be detachable. If the suspension chamber is connected to the medium chamber and a sample is inserted into the sample holder, then the sample is arranged as a boundary surface between the suspension chamber and the medium chamber.

In an alternative embodiment, the medium chamber and the suspension chamber can be designed as a contiguous component into which the sample holder is inserted in such a manner that the sample forms a boundary between the medium chamber and the suspension chamber.

In one implementation of the embodiment, the suspension chamber has a suspension chamber vent line which is arranged on a side of the suspension chamber which faces away from the sample holder. Similarly to the vent line of the medium chamber, which is advantageously positioned for filling the medium chamber with the culture medium, the suspension chamber vent line is arranged on the side of the suspension chamber which faces away from and/or is opposite the sample holder. This arrangement of the suspension chamber vent line enables a complete filling of the suspension chamber with a suspension when the suspension chamber vent line is located vertically above the sample holder. In this case, the suspension chamber vent line can be arranged, for example in the above-described suspension filling position, at the vertically highest point of the suspension chamber, and the sample holder can be arranged substantially at the vertically lowest point of the suspension chamber.

According to one embodiment, at least one transparent region is formed in a lateral wall of the medium chamber. The region is transparent to light and is used for observing the culture medium arranged in the medium chamber. A growth and thus contamination of the medium chamber can be detected via the transparent region. In particular, two opposing transparent regions can be formed in the medium chamber, such that a contamination of the medium chamber can be detected using the light penetrating the medium chamber. To detect a discoloration and/or darkening of the culture medium, a contamination probe can be included which automatically checks the contamination on the transparent region.

According to one embodiment, the sample holder is arranged and/or coupled to the medium chamber in a detachable connection. If the sample holder is detached from the medium chamber, the sample can be inserted into the sample holder, for example, and/or the sample can be subjected to a physical integrity test, such as the application of pressure or voltage. The sample holder in this case is designed in such a manner that the sample is also held securely by the sample holder, if the same is separate from the medium chamber—and optionally the suspension chamber.

The physical integrity test of the sample can also be carried out in one embodiment if the sample holder is coupled to the medium chamber and/or the suspension chamber.

According to one embodiment, the device is constructed to be stable under a vacuum of about 1×10-10 mbar, up to an overpressure of about 2 bar. The values given are minimum values. The device can particularly remain dimensionally stable even at lower pressures (greater vacuum), or at higher overpressures. To this end, the device can be at least partially constructed of stainless steel and/or a suitable plastic. Transparent regions can be constructed of glass, acrylic glass and/or a transparent plastic. The pressure-stable construction of the device enables an application of pressure and/or vacuum to the sample inserted into the device, for example as part of a physical integrity test and/or for an application of a contaminated suspension and/or a contaminated aerosol under pressure. In addition, the medium chamber can be placed under pressure with or without culture medium, as can optionally be the suspension chamber, which can be filled with a suspension. During pressurization, the sample remains securely and tightly clamped in the sample holder.

According to one embodiment, the device is constructed to be temperature-stable at a temperature of −50° C. to +100° C. For this purpose, the device can be constructed, by way of example, at least partially of stainless steel and/or a suitable plastic.

According to one embodiment, the device has an electrode for making contact with the inner chamber of the medium chamber. The electrode is used for electrically and physically contacting a culture medium arranged in the medium chamber. A further electrode can optionally be provided for contacting the inner chamber of the suspension chamber. The electrodes are used to measure electrical currents in the culture medium, in the suspension, and/or between the inner chamber of the medium chamber and the suspension chamber inner chamber. In this case, currents can arise in the culture medium if the culture medium is contaminated. In this case, the electrode is used to detect a contamination. For this purpose, electrical connections of the electrode, as well as further electrodes, can be included on a current- and/or voltage measuring device.

In one embodiment, inlet lines and/or outlet lines of the device can have a closable design. The inlet lines and outlet lines are used for inflow and outflow of fluid, and can be tubular in design, and can be clamped off by, for example, an external hose clamp that can be placed on the outside of the inlet line and/or outlet line. As such inlet lines and outlet lines, the device can comprise on the same, for example: a medium inlet line for the filling of the medium chamber with a culture medium, a medium outlet line for discharging the medium chamber, a medium sample withdrawal point for withdrawing a sample from the medium chamber, the vent line, a suspension inlet line for admitting a suspension into the suspension chamber, a suspension outlet line for emptying the suspension chamber, a suspension sample withdrawal point for withdrawing a sample from the suspension chamber, and/or the suspension chamber vent line. For closing the inlet lines and outlet lines, one or more seals can be provided.

A second aspect relates to a method for carrying out an integrity test on a sample of disposable components, comprising the steps of:
providing a medium chamber with an inner chamber which is bounded to the outside;
arranging the sample in a sample holder in such a manner that the sample at least partially bounds the medium chamber to the outside;
orienting the medium chamber in a filling position such that a vent line of the medium chamber is substantially arranged at the highest point of the inner chamber of the medium chamber; and
filling the inner chamber of the medium chamber with a culture medium, with the vent line open.

Subsequently, a bacteria challenge test (BCT) can be carried out, in which the culture medium filled into the medium chamber is used to check the integrity of the sample.

In one method step, the sample can be separated from a disposable component. In the filling position, the medium chamber is vented via the vent line at its highest point with respect to the earth. This provides a particularly favorable option for venting the medium chamber, wherein the medium chamber can be completely filled with the culture medium. When the inner chamber of the medium chamber is filled with the culture medium, the medium chamber is vented via the vent line arranged at top. Particularly, in the filling position, the vent line can be arranged substantially vertically above the sample holder, wherein the vent line can be constructed on a side of the medium chamber facing away from the sample holder.

According to one embodiment, the method comprises the steps of:
orienting the medium chamber in an application position, in which the sample is oriented with an inclined outer sample surface, and
applying bacteria and/or spores from outside to the sample in the application position.

The application can be carried out with a suspension and/or with an aerosol which contain(s) the bacteria and/or spores. In the application position, the sample constitutes a boundary surface of the medium chamber which provides a substantially inclined boundary surface and/or application surface of the medium chamber for the application of bacteria and/or spores to the sample. The bacteria are able to act on the inclined outer sample surface particularly well, which enables an efficient and intensive stressing of the sample during the integrity test. 'Inclined' in this case means that the outer sample surface is inclined relative to a horizontal plane—i.e., is particularly oriented vertically.

In one implementation of this embodiment, a bacteria and/or spore aerosol is applied directly in the suspension filling position, and can be at least partially deposited on the sample. To this end, the medium chamber, along with the sample, can be positioned in an aerosol chamber in which the aerosol is arranged. Aerosol which is deposited on the sample is particularly suitable for the verification of the integrity of the sample. Additionally, the aerosol can be presented under pressure. That is, the aerosol can be applied to the sample under pressure. For this purpose, the entire aerosol chamber can be pressurized.

In an alternative or additional implementation of this embodiment, the method is carried out with the steps:
  providing a suspension chamber in such a manner that a suspension chamber inner chamber is at least partially separated from the inner chamber of the medium chamber only by the sample arranged in the sample holder, and
  orienting the device in a suspension filling position in such a manner that a suspension chamber vent line is arranged substantially at the highest point of the suspension chamber inner chamber,
  filling a suspension chamber inner chamber in the suspension filling position with a bacteria and/or spore suspension, with the suspension chamber vent line open.

The suspension chamber enables an application of a contaminated suspension to the sample. The suspension in this case can be directly applied to the sample during the integrity test. When the chamber is filled with the suspension, the suspension chamber is vented upwards via the suspension chamber vent line, which enables a complete filling of the suspension chamber. The suspension chamber vent line can be arranged on the side of the suspension chamber facing away from the sample holder. In the suspension filling position, the medium chamber can be oriented in such a manner that the sample at least partially bounds the medium chamber vertically upwards.

One aspect relates to the use of a device according to the first aspect, for carrying out an integrity test on a sample of disposable components according to a method according to the second aspect.

The invention is described below in greater detail with reference to embodiments shown in the figures.

BRIEF DESCRIPTION OF THE DRAWINGS

FIGS. 1A-1C show, in schematic representations, a device for carrying out an integrity test, with a sample placed on a medium chamber, wherein

FIGS. 2A-2C show, in schematic representations, the device illustrated in FIGS. 1A-1C, with a suspension chamber placed thereon, wherein

DETAILED DESCRIPTION

Figure 1A:
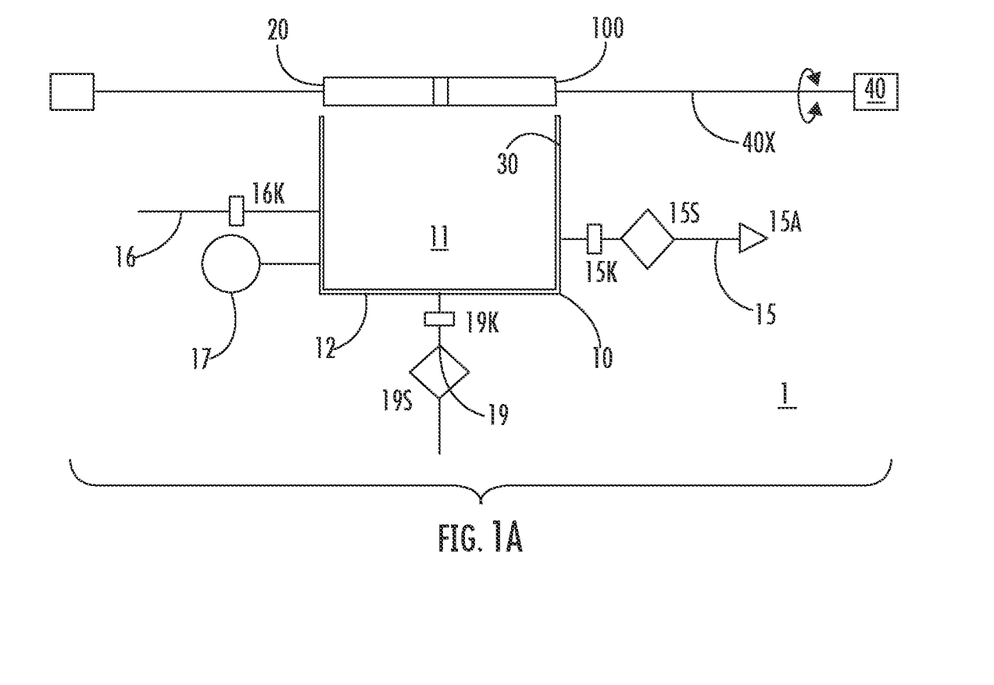
FIG. 1A shows the medium chamber aligned with but spaced from a sample holder.
Figure 1B:
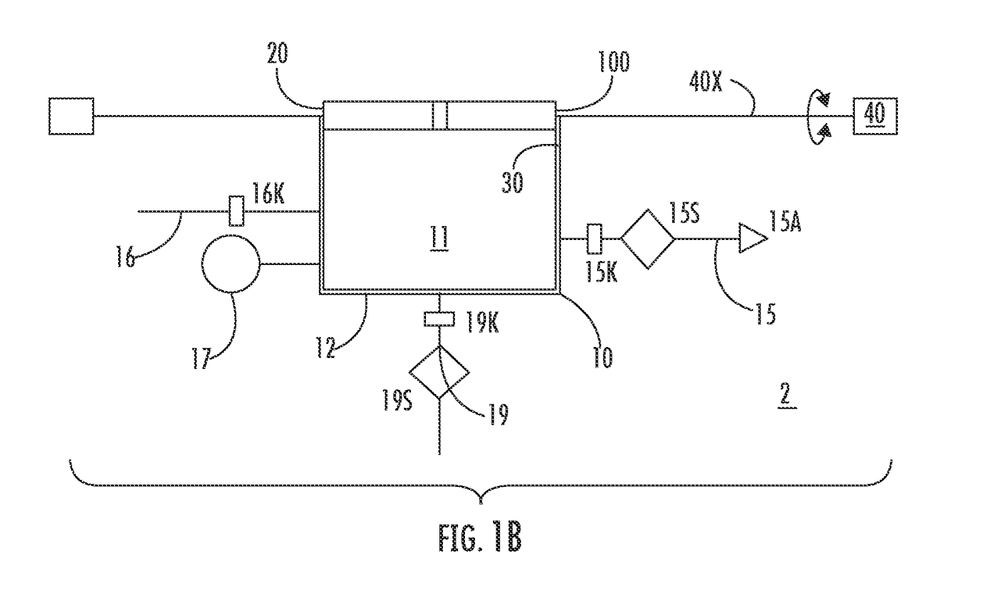
FIG. 1B shows the medium chamber mounted to the sample holder and FIG. 1C shows the sample holder and the medium chamber rotated so that a vent of the medium chamber is above the sample holder.
Figure 1C:
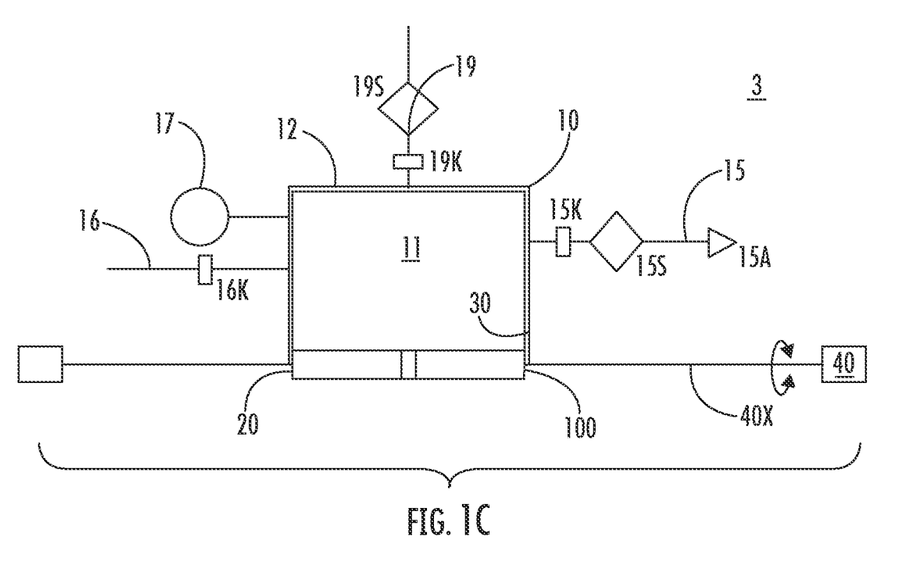

FIGS. 1A-1C show, in schematic representations, a device for carrying out an integrity test on a sample of disposable components. The device 1 has a medium chamber 10, the lateral walls 12 of which define and enclose an inner chamber of the medium chamber—the medium chamber inner chamber 11. A lateral wall of the medium chamber 10 is formed by a sample 100. The sample 100 is arranged in a sample holder 20.

A disk-shaped sample of a disposable component for the biopharmaceutical industry can be used as a sample. The sample can consist of a punched-out piece of film and/or foil. The sample 100 is substantially flat in form. This sample 100 arranged in the sample holder 20 bounds the medium chamber inner chamber 11 to the outside by means of this surface. The sample 100 in this case can be disk-shaped in form, for example, and can be designed as a cylinder cover of a cylindrical medium chamber 10. In another embodiment, the sample can substantially be in the form of a square or rectangular surface. The diameter and/or the diagonal of the sample 100 in these cases preferably is 20 mm to 100 mm, in particular 40 mm to 70 mm, and more preferably 50 mm. The volumetric shape of the medium chamber 10 can be adapted to a predetermined sample shape—for example, as described above, a disk-shaped, a rectangular, a square or an elliptical shape. The sample 100 can be arranged in the sample holder 20 in such a manner that it forms a cover of the medium chamber 10—for example a cylinder cover of a cylindrical medium chamber or a rectangular cover a box-shaped medium chamber.

The medium chamber 10 is designed and intended to receive a culture medium such as TSB. For this purpose, the medium chamber 10 has at least one medium inlet line 15. Optionally, the medium chamber 10 can have a medium outlet line 16, out of which a medium such as a culture medium can be discharged from the medium chamber 10.

The lines shown in the figures can be designed in one embodiment as integral components of the chamber wall. The lines in this case require little constructed space in the radial orientation, and contain very little culture medium. As such, a bacterial growth takes place in a targeted manner only in the medium chamber and not (or only to a very limited degree) in the adjoining lines.

A vent line 19 is arranged in the lateral wall 12 of the medium chamber 10 which is opposite the sample 100 and/or the medium chamber inner chamber 11. The vent line 19 is constructed on the side of the medium chamber 10 facing away from the sample holder 20. The vent line 19 serves to vent the medium chamber inner chamber 11. The vent line 19 can be closed and opened by means of a vent line clamp 19K. In addition, a vent line sterile filter 19S is arranged in the vent line 19. The vent line sterile filter 19S is used to keep sterile the vent line 19, in order to prevent accidental contamination of the medium chamber 10 after the sterilization.

For this purpose, all lines can have corresponding sterile barriers. This serves to prevent any prior contamination during sample preparation, such that only a deliberate contamination by the sample can take place during the integrity test.

All inlet lines and outlet lines of the device 1, and in particular of the medium chamber 10, are designed as sterile connections. Thus, the medium inlet line 15 either has a medium inlet line sterile filter 15S, a medium inlet line aseptic connector 15A, a medium inlet line septum, or a combination thereof. The medium inlet line 15 further has a medium inlet line clamp 15K for closing and opening the medium supply line 15. The medium outlet line 16 also has a medium outlet line clamp 16K for opening and closing the medium outlet line 16.

The clamps above can be designed, by way of example, as external hose clamps, which can be opened and closed either by hand by a user, or in an automated manner.

The sample holder 20 serves to hold the sample 100 in such a manner that the sample forms a lateral wall of the medium chamber 10. The sample holder 20 can be designed, for example, as a clamping device. The sample holder 20 connects the sample 100 in a medium-tight and sterile manner to the medium chamber 10—for example via flat seals and/or O-rings.

The medium chamber 10 can furthermore comprise a medium sample withdrawal point 17, via which a sample of the culture medium in the inner chamber 11 of the medium chamber 10 can be removed. The medium sample withdrawal point 17 can be designed, by way of example, as a septum. By removing a medium sample of the culture medium, it is possible to check for a contamination of the culture medium contained in the medium chamber 10.

The device 1 can be constructed entirely or partially of stainless steel and/or plastic. If the device is made of stainless steel, two opposing transparent viewing windows are preferably formed in the medium chamber 10, via which a discoloration and/or clouding of the culture medium can be detected. In the plastic design of the device 1, the device is preferably constructed from a transparent plastic. Each transparent region allows simple monitoring of bacterial growth in the medium chamber 10. The device is constructed of a sterilizable material—i.e., a material that withstands sterilization by autoclaving, steaming with hot steam, gamma radiation and/or EtOH gassing.

The device 1 further comprises an orienting device 40. The orienting device 40 is used for orienting the medium chamber 10 in such a manner that the vent line 19 attaches to a point of the medium chamber 10 which is arranged above the sample 100. The orienting device 40 can particularly comprise a pivot axis, which is shown by the line 40x in FIGS. 1A-1C. The pivot axis 40x of the orienting device 40 can engage with the sample holder 20, and orient the device 1 by pivoting the sample holder 20 and the medium chamber 10 connected to the sample holder 20.

To fill the medium chamber 10 with a culture medium, the medium chamber 10 is pivoted by means of the orienting device 40 via the sample holder 20. In this filling position, the inner chamber 11 of the medium chamber 10 is arranged above the sample holder 20 and therefore also above the sample 100, as shown in FIG. 1C. The sample 100 forms the base surface of the medium chamber 10 in the filling position. In the filling position, the vent line 19 is constructed on the lateral wall 12 of the medium chamber which forms the roof and/or the cover of the medium chamber 10. In the filling position, the medium chamber 10 can be filled particularly easily and free of bubbles with a culture medium which is conveyed via the medium inlet line 15 into the inner chamber 11 of the medium chamber 10.

The lateral wall 12 of the medium chamber 10 where the vent line attaches 19 can be designed in such a manner that it tapers toward the attachment point of the vent line 19. This tapering shape further improves the filling process for the medium chamber 10 and ensures a complete filling of the medium chamber 10.

The orienting device 40 enables orienting of the device 1 in different positions. Specifically, the orienting device 40 enables orienting the device 100 in such a manner that the sample 100 is oriented substantially horizontally or with an inclined outer sample surface. For the horizontal orientation of the sample 100, there are two different options: on the one hand, the filling position described above and shown in FIGS. 1C and 1n FIG. 2C, in which the inner chamber 11 of the medium chamber 10 is arranged above the sample 100; and on the other hand, a suspension filling position, which is shown in FIGS. 1B, 2A and 2B and in which the sample 100 is arranged above the inner chamber 11 of the medium chamber 10.

Figure 2A:
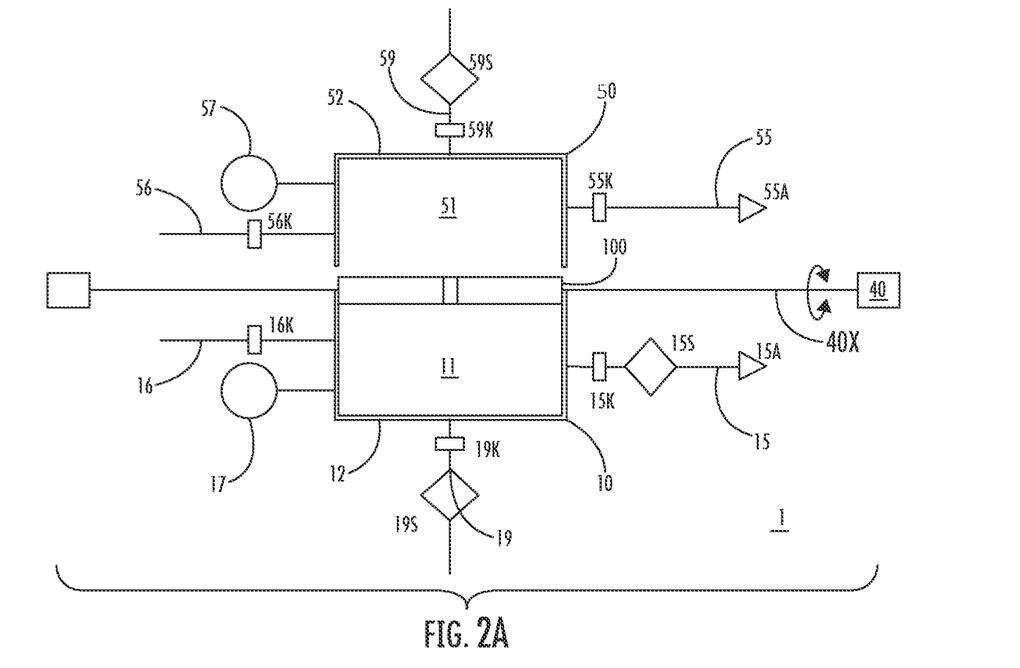
FIG. 2A shows the suspension chamber aligned with but spaced from a sample holder.
Figure 2B:
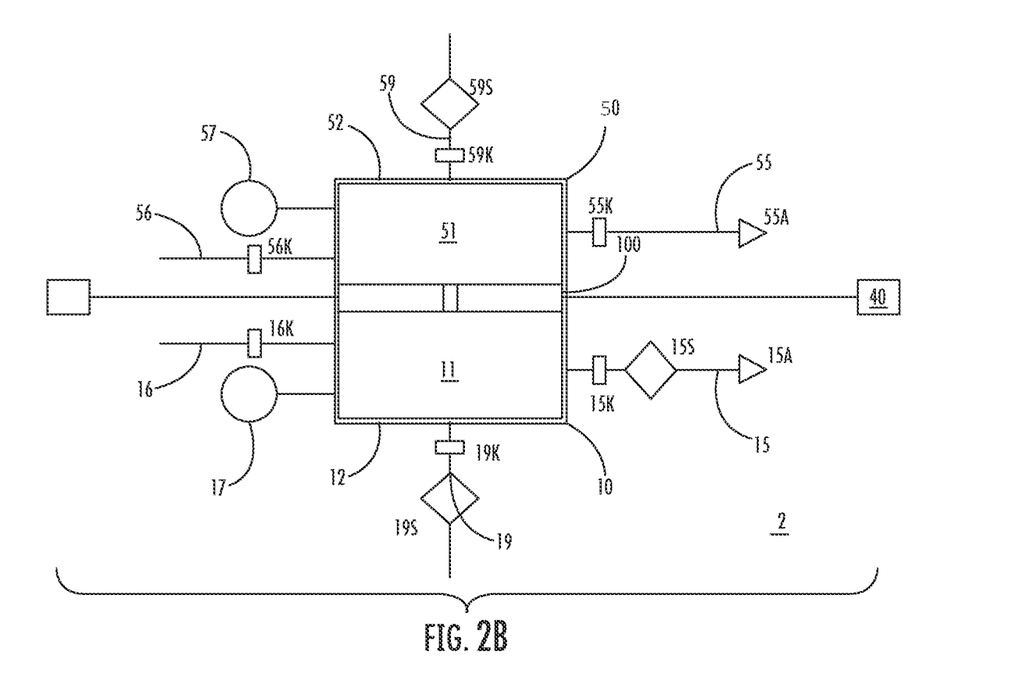
FIG. 2B shows the suspension chamber mounted to the sample holder and rotated so that a vent of the suspension chamber is above the sample holder and FIG. 2C shows the sample holder, the medium chamber and the suspension chamber rotated so that a vent of the medium chamber is above the sample holder.
Figure 2C:
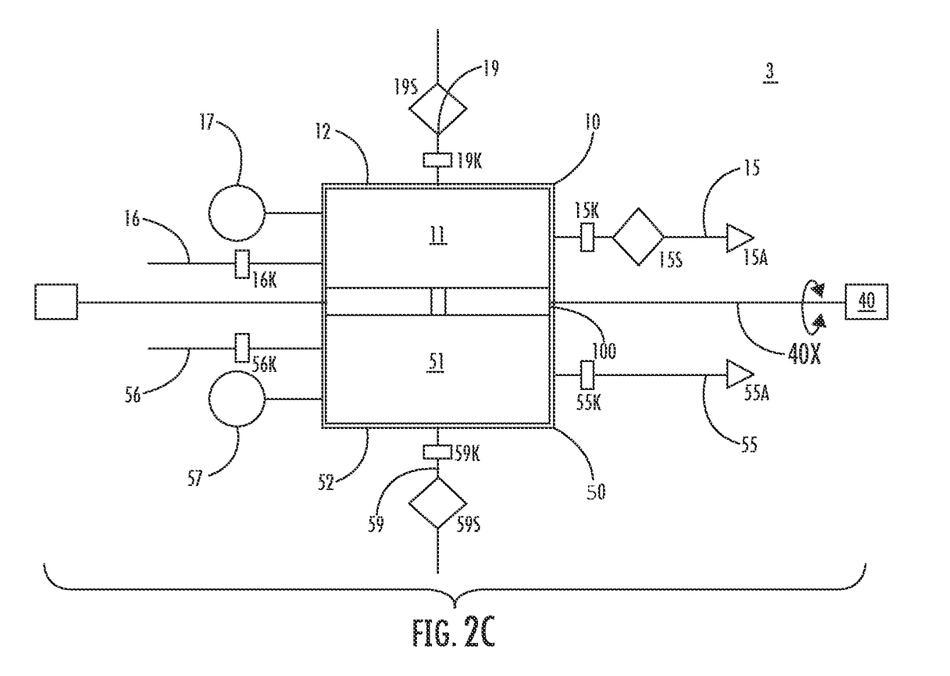

FIG. 2A shows the device shown in FIGS. 1A-1C with a suspension chamber 50 aligned with a side of the filter holder 20 opposite the side to which the medium chamber 10 is attached, but with the suspension chamber 50 spaced from the filter holder 20, FIG. 2B shows the suspension chamber 50 that has been attached to the filter holder 20 and FIG. 2C shows the attached suspension chamber 50 rotated so that the vent line 19 of the medium chamber 10 is above the sample holder 20. The suspension chamber 50 serves to receive a contaminated suspension, wherein bacteria and/or spores can be filled into the same for the purpose of checking the integrity of the sample 100.

The suspension chamber 50 has a suspension chamber inner chamber 51 which is bounded to the outside by suspension chamber lateral walls 52. A lateral wall of the suspension chamber 50 is formed by the sample 100 which is arranged in the sample holder 20. In the position shown in FIGS. 2B and 2C, the sample 100 is configured as a boundary surface between the inner chamber 11 of the medium chamber 10 and the suspension chamber inner chamber 51 of the suspension chamber 50. The suspension chamber 50 and the medium chamber 10 are arranged on opposite lateral surfaces of the sample 100. In this case, the medium chamber inner chamber 11 is arranged on an inner sample surface of the sample 100, and the suspension chamber inner chamber 51 is arranged on an outer sample surface of the sample 100.

Both the suspension chamber 50 and the medium chamber 10 are detachably connected to the sample holder 50. For this purpose, the sample holder 20 can have connecting elements such as a threading, snap-in elements, or plug elements, which are designed and intended for connection to the medium chamber 10 and/or the suspension chamber 50. Accordingly, the medium chamber 10 and/or the suspension chamber 50 can comprise complementary connecting elements for connecting to the connecting elements of the sample holder 20. The connection between the sample holder 20 and the medium chamber 10 is medium-tight and sterilizable. The connection between the sample holder 20 and the suspension chamber 50 can also be medium-tight and sterilizable in design.

The initially detachable connection between the sample holder and the medium chamber and/or suspension chamber can be permanently fixed, for example by gluing and/or extrusion. A permanently fixed connection reduces, for example, the risk of accidental contamination.

Alternatively, the medium chamber 10 and the suspension chamber 50 can also be designed to be able to directly connect to each another via a connecting element (30). In this embodiment, the sample arranged in the sample holder can be inserted between the two chambers in such a manner that the sample forms a boundary surface between the respective inner chambers.

As shown in FIGS. 2A-2C, the suspension chamber 50 can be designed substantially with mirror symmetry to the medium chamber 10, and have corresponding dimensions and shapes.

In the suspension chamber lateral wall 52 which is arranged opposite the sample holder 20, the suspension chamber 50 has a suspension chamber vent line 59 with a suspension chamber vent line clamp 59K for closing and opening the suspension chamber vent line 59. In addition, the suspension chamber vent line 59 has a suspension chamber vent line sterile filter 59S for the sterilization of the line.

Analogously to the medium chamber 10, the suspension chamber 50 can have a suspension inlet line 55 with a suspension inlet line aseptic connector 55A and a suspension inlet line clamp 55K. In addition, the suspension chamber 50 can be connected to a suspension outlet line 56 for discharging the suspension from the suspension chamber inner chamber 51, which can be closed and opened by a suspension outlet line clamp 56K. A suspension sample withdrawal point 57 is used for withdrawing a sample of the suspension, and can optionally be included. The suspension sample withdrawal point 57 can be designed as a septum.

In the above-described suspension filling position of the device 1, in which the device 1 is shown in FIG. 2B, the suspension chamber inner chamber 51 can be completely filled via the suspension inlet line 55 with a suspension. In the suspension filling position of FIG. 2B, the suspension chamber vent line 59 is arranged at the upper end of the suspension chamber 50, which enables a complete venting of the suspension chamber inner chamber 51. The suspension chamber lateral wall 52 where the suspension chamber vent line 59 attaches can be designed with a tapered cross section which tapers towards the attachment point of the suspension chamber vent line 59.

The vent line 19 of the medium chamber 10 and the suspension chamber vent line 59 are arranged on opposite ends of the device 1. All other inlet lines and outlet lines can also be arranged on lateral walls of the device. To limit the horizontal dimensions of the device 1, all inlet lines and outlet lines (otherwise than in the figures) can attach to the two lateral walls to which are attached the vent line 19 and the suspension chamber vent line 59—that is, to the lateral walls which bound the device 1, in the filling position and in the suspension filling position, at their vertical ends.

Figure 3A:
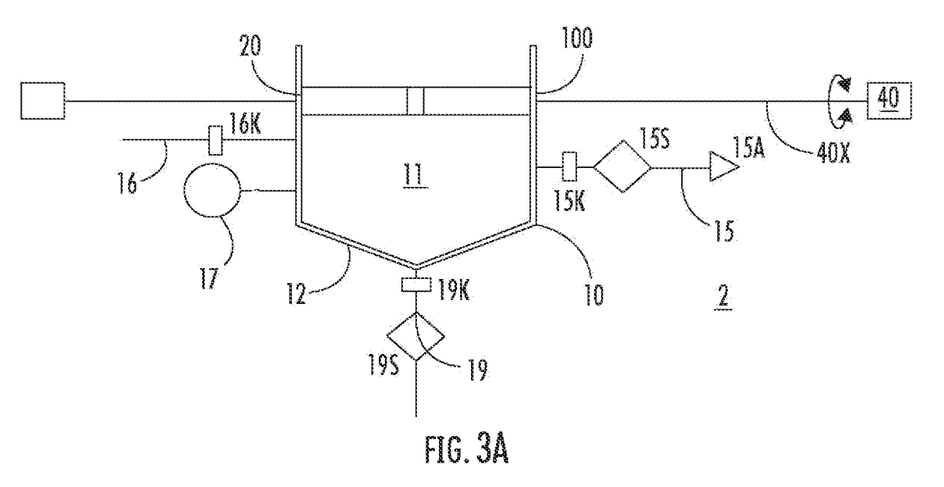
FIGS. 3A to 3D each show, in a schematic representation, an embodiment of a device for carrying out an integrity test, with a sample placed on a medium chamber.

FIG. 3A shows an embodiment of a device 2, wherein the lateral wall 12 of the medium chamber 10 which faces away from the sample holder 20 is designed with a cross section which tapers with increasing distance from the sample holder 20. The vent line 19 is arranged at the position of the side of the medium chamber 10 which faces away from the sample holder which has the smallest cross-section. The vent line 19 is arranged in the device 2 shown in FIG. 3A centrally on the side of the medium chamber 10 which faces away from the sample holder 20.

Figure 3B:
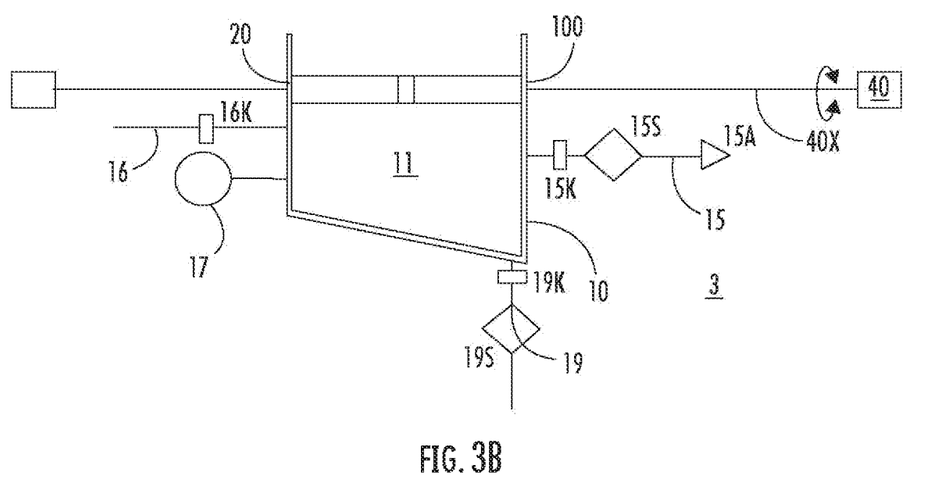

FIG. 3B shows an embodiment of a device 3 in which the lateral wall 12 of the medium chamber 10 which faces away from the sample holder 20 is—as in the device 2—designed with a cross section which tapers with increasing distance from the sample holder 20. In the device 3, the vent line 19 is arranged decentrally on the side of the medium chamber 10 facing away from the sample holder 20.

In the devices 2 and 3 shown in FIGS. 3A and 3B, the vent line 19 is arranged in such a manner that it runs away from the medium chamber 10, and is oriented substantially parallel to a normal on the sample 100.

Figure 3C:
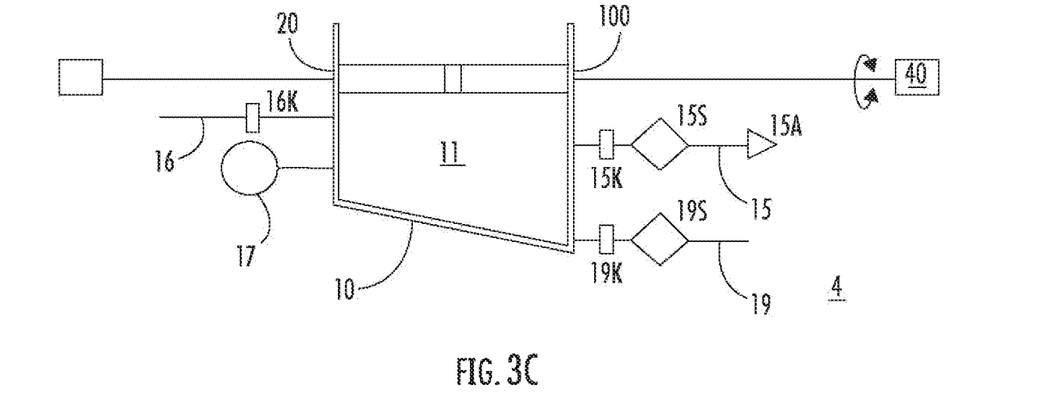

FIG. 3C shows an embodiment of a device 4 in which the lateral wall 12 of the medium chamber 10 which faces away from the sample holder 20 is also designed with a cross section which tapers with increasing distance from the sample holder 20, similar to device 3. In contrast to device 3, the vent line 19 attaches at the point of the inner chamber 11 of the medium chamber 10 which is farthest from the sample holder 20, and thus from the sample 100, but does not run perpendicular to, but rather substantially parallel to, the sample 100.

Alternatively, the vent line 19 could also be arranged in such a manner that it runs at an angle from the sample 100 and substantially away from the medium chamber 10.

Figure 3D:
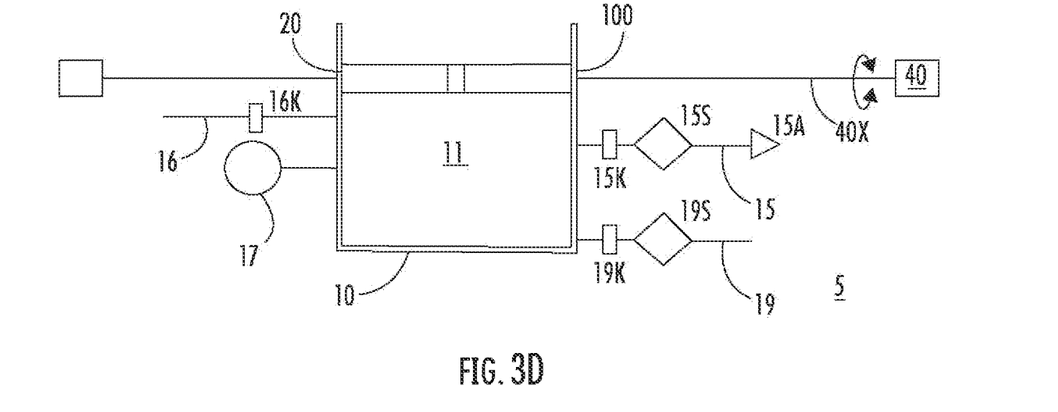

FIG. 3D shows an embodiment of a device 5 in which the lateral wall 12 of the medium chamber 10 opposite the sample holder 20 is constructed substantially parallel to the sample. The vent line 19 in this case is attached to a lateral wall of the medium chamber 10 which itself is not opposite the sample holder 20, but rather adjoins the sample holder 20. In this case, the vent line 19 is directly adjacent to the opposite lateral wall 12 of the medium chamber 20. Also in device 5, the vent line 19 is therefore constructed on the side of the medium chamber 10 facing away from the sample holder 20.

The devices 2 through 5 shown in FIGS. 3A to 3D are each shown without a suspension chamber 50. The devices 2 through 5 can each have connecting elements for connection to a suspension chamber 50, which can be designed, by way of example, with mirror symmetry to the medium chamber 10 with respect to the sample 100 placed in the sample holder 20, as shown in FIG. 2 for device 1.

With the device, an integrity test of a sample can be carried out, specifically with the method described below:

Method for Carrying Out an Integrity Test on a Sample of Disposable Components

A method for carrying out an integrity test on a sample of disposable components can be carried out with the device 1 shown in the figures. The method can be carried out with some or all of the method steps listed below. Individual method steps can be omitted. In addition, the method can include carrying out further method steps. The method steps can be carried out, by way of example, in the order listed below. However, individual method steps can be carried out in advance and/or later.

Step a: inserting the sample 100 into the sample holder 20.

Step b: carrying out a physical integrity test.

The physical integrity test can be carried out as a part of the integrity test to be carried out in total. In the physical integrity test, the sample can be checked for physical load capacity and/or for an existing leak. The physical integrity test of the sample 100 can be carried out without the medium chamber 10 and without the suspension chamber 50—that is, only on the sample 100 inserted into the sample holder 20. Alternatively, the physical integrity test can be carried out with the medium chamber 10 attached to the sample holder 20 and/or the suspension chamber 50 attached to the sample holder 20. In this case, the medium chamber 10 can be tightly closed, with the exception of the vent line 19. All lines on the suspension chamber are open to gas flows in this case, optionally via their respective sterile barriers. A measuring instrument can be connected to the vent line 19 and/or to the suspension chamber vent line 59 for the purpose of carrying out the physical integrity test. A pressure drop 
measurement method or a gas detection method can be used as a possible test method of the physical integrity test—the latter, for example, with carbon dioxide, inert gas, nitrogen, SF6 and/or helium as a test gas.

Step c: providing the medium chamber 10 with an inner chamber 11 which is bounded to the outside.

Step d: arranging the sample 100 in a sample holder 20 in such a manner that the sample 100 at least partially bounds the medium chamber 10 to the outside;

The medium chamber 10 in this case can be connected to the sample holder 20, assuming these were not already connected to each other previously.

Step e: sterilization of the device 1, for example by autoclaving, steaming with superheated steam, gamma radiation and/or EtOH-gassing.

Step f: orienting the medium chamber 10 in the filling position such that the vent line 19 of the medium chamber 10 is arranged substantially at the highest point of the inner chamber 11 of the medium chamber 10.

In the filling position, the internal space 11 of the medium chamber 10 is arranged substantially vertically above the sample 100, which in the filling position at least partially forms the base of the medium chamber 10. The vent line 19 in this case can be arranged substantially vertically above the sample holder 20, wherein the vent line 19 is arranged on the side of the medium chamber 10 facing away from the sample holder 20.

Step g: filling the inner chamber 11 of the medium chamber 10 with a culture medium, with the vent line 19 open.

In this case, the medium chamber 10 can be filled with the culture medium to such an extent that the culture medium rises above the vent line clamp 19K. Subsequently, all blocking devices on all inlet lines and outlet lines can be closed—i.e., in particular the vent line clamp 19K, the medium inlet line clamp 15K, and the medium outlet line clamp 16K. In this way, the medium chamber 10 is completely filled with the culture medium.

The culture medium can be connected via prepared bags and/or syringes to the medium inlet line 15. This coupling of the culture medium to the medium inlet line 15 can occur prior to the sterilization in method step e.

Step h: carrying out a first incubation phase.

Here, the device 1 can be observed under suitable cultivation conditions for a predetermined period of time and analyzed for microbiological growth. The predetermined period of time of the first incubation period can be, e.g., at least seven days. The review during the first incubation phase can be done, for example, by sampling at the medium sample withdrawal point 17, or by observation through a transparent region of the lateral wall 12 of the medium chamber 10. A verification is made as to whether microbiological growth of the culture medium takes place in the medium chamber 10 with no particular exposure to bacteria and/or spores, which points to a contamination of the culture medium through the sample 100, or to an insufficient sterilization of the device.

The method is described at this point in an embodiment in which the device 1 is used together with the suspension chamber 50. Alternatively, the method can, starting from this method step h, be carried out without the use of a suspension chamber 50, which will be described further below in an alternative embodiment of the method.

Step i: providing the suspension chamber 50 in such a manner that the suspension chamber inner chamber 51 is at least partially separated from the inner chamber 11 of the medium chamber 10 only by the sample 100 arranged in the sample holder 20.

If the suspension chamber 50 was not previously connected to the device 1, the provision of the suspension chamber can include connecting the suspension chamber 50 to the device 1, in particular by a connection to the sample holder 20 and/or the medium chamber 10. If the suspension chamber is attached subsequently, it should have been additionally sterilized separately—for example in a Tyvek pouch with a sterile barrier, so as not to contaminate the suspension chamber during intermediate storage.

The handling of all parts of the device, up to the attachment of the suspension chamber after the sterilization, is preferably carried out on a Cleanbench. Otherwise, the contamination could occur with a different organism than the test organism. In this case, the test organism could be documented additionally.

The suspension chamber inner chamber 51 is arranged above the sample 100 in the suspension filling position.

Step j: orienting the device 1 in a suspension filling position in such a manner that a suspension chamber vent line 59 is arranged substantially at the highest point of the suspension chamber inner chamber 51.

In the suspension filling position, the inner chamber 11 of the medium chamber 10 is arranged substantially below the sample 100. In this case, the sample 100 at least partially bounds the medium chamber 10 vertically upward.

Step k: filling the suspension chamber inner chamber 51, in the suspension filling position, with a bacteria and/or spore suspension, with the suspension chamber vent line 59 open.

The suspension chamber 50 in this case can be filled beyond the suspension chamber vent line clamp 59K with the suspension. Subsequently, all blocking devices on all inlet lines and outlet lines can be closed—i.e., in particular the suspension chamber vent line clamp 59K, the suspension inlet line clamp 55K, and the suspension outlet line clamp 56K. In this way, the suspension chamber 50 is completely filled with the suspension. The suspension chamber vent line 59 can be arranged on the side of the suspension chamber 50 facing away from the sample holder 20.

The suspension can be connected to the suspension feed line 55 via prepared pouches and/or syringes. The suspension can be designed as a suspension containing bacteria and/or spores, for a suspension BCT.

Step l: orienting the sample 100 in a predetermined application position.

The predetermined application position may coincide with the suspension filling position. In the application position, the sample can be alternatively oriented substantially vertically.

Step m: holding the sample 100 for a predetermined residence time in the application position, in such a manner that the suspension solution is applied to the full surface of the sample 100.

The predetermined residence time can be from 10 minutes to 200 minutes. In this case, pressure can optionally be applied to one side of the device 1—for example, a pressure of up to 2 bar. The single-sided application of pressure can be implemented, by way of example, either on the side of the medium chamber 10 or on the side of the suspension chamber 50, via the respective vent line 19 and/or 59.

Furthermore, during method step m, a (for example, additional) physical integrity test can be carried out, for example by measuring a volume resistivity and/or the conductivity via, in each case, one electrode which contacts the inner chamber 11 of the medium chamber 10 and one electrode that contacts the suspension chamber inner chamber 51.

Step n: orienting the device 1 by means of the orienting device 40 in such a manner that the suspension outlet line 56 is arranged at the lowest point of the suspension chamber inner chamber 51.

Step o: completely emptying the suspension chamber 50.

Step p: rinsing the suspension chamber 50, for example by an overflowing rinse with ultrapure water.

Step q: completely emptying the suspension chamber 50.

Step p: optionally drying the suspension chamber 50, for example by a flow of compressed air.

Step r: carrying out a second incubation phase.

Here, the device 1 can be observed under suitable cultivation conditions for a predetermined period of time and analyzed for microbiological growth. The predetermined period of time of the second incubation phase can be, e.g., seven to 21 days. The verification during the second incubation phase can be done, for example, by sampling at the medium sample withdrawal point 17, and/or by observation through a transparent region of the lateral wall 12 of the medium chamber 10. A verification is made as to whether microbiological growth of the culture medium takes place in the medium chamber 10 with no particular exposure to bacteria and/or spores, which points to a contamination of the culture medium through the sample 100. For final verification, the culture medium can also be completely discharged from the medium chamber 10 and then verified.

Upon detection of a contamination of the medium chamber, the sample has not passed the suspension BCT as a part of the integrity test.

Alternative Embodiment of the Method

Alternatively, the method can be continued with the steps i to r following the first incubation phase (step h), with some or all of the following method steps:

Step s: orienting the sample 100 in a predetermined application position.

The predetermined application position may coincide with the suspension filling position. In the application position, the sample can be alternatively oriented substantially vertically.

Step t: inserting the device 1 into an aerosol chamber.

The aerosol chamber is provided and designed for aerosolization as part of an aerosol BCT, and additionally to house the device 1 (optionally also a plurality of devices 1). The device 1 can be used in this case without the suspension chamber 50—that is, as in the embodiment shown schematically in FIG. 1. Optionally, the suspension chamber 50 can be detached from the device 1 prior to step t.

Step u: holding the sample 100 for a predetermined residence time in the application position such that an aerosol in the aerosol chamber is applied to the full area of the sample 100.

The predetermined residence time can be from 10 minutes to 200 minutes. During the predetermined residence time, the aerosol contained in the aerosol chamber has a predetermined concentration. Optionally, the sample is therefore held in the aerosol chamber additionally to the predetermined residence time during an initial phase in which a predetermined minimum concentration of the aerosol is provided. The aerosol is designed as a bacteria and/or spore aerosol for carrying out a BCT.

The sample 100 in this case can be oriented in the application position horizontally, for example, with the sample upward—or in an alternative embodiment, substantially vertically with an inclination to the horizontal.

In this case, pressure can optionally be applied to one side of the device 1—for example, a pressure of up to 2 bar. The single-sided application of pressure can be implemented, by way of example, via the vent line 19 of the medium chamber 10.

Step v: removing the device 1 together with the sample 100 from the aerosol chamber.

Alternatively, the aerosol chamber can also be cleaned by the aerosol.

Step w: rinsing the sample 100, for example by an overflowing rinse with ultrapure water.

Step x: optionally drying the sample 100, and possibly the suspension chamber 50, for example by a flow of compressed air.

Step y: carrying out a second incubation phase.

As described in the first embodiment of the method, the device 1 can be observed under suitable cultivation conditions for a predetermined period of time, and analyzed for microbiological growth. The predetermined period of time of the second incubation phase can be, e.g., seven to 21 days. The verification during the second incubation phase can take place, e.g., by sampling at the medium sample withdrawal point 17, by observation through a transparent region of the lateral wall 12 of the medium chamber 10, and/or by voltage or current measurement via a measuring electrode. A verification is made in this case as to whether bacteria and/or spores produce a microbiological growth of the culture medium in the medium chamber 10, which points to a contamination of the culture medium through the sample 100. For final verification, the culture medium can also be completely discharged from the medium chamber 10 and then verified.

During the second incubation phase, a sterilized cover, which is attached after the drying, can be attached to the outside of the sample. The risk of cross-contamination during further handling is minimized in this way. The cover can also be attached on a Cleanbench, for example.

Upon detection of a contamination of the medium chamber, the sample has not passed the aerosol BCT as a part of the integrity test.

Further Alternatives of the Method

Following the second incubation phase (according to method step r and/or method step y), the medium chamber 10 can be completely emptied, for example analogously to the method steps n to p for emptying the suspension chamber 50.

The methods described above can be varied in many ways. As such, in some embodiments, the first incubation according to step h can be omitted. In this case, the sterilization of the device 1 and the medium-tight attachment of the sample 100 to the medium chamber 10 are not verified by means of the first incubation phase.

In addition, both a suspension BCT according to method steps i to r, and an aerosol BCT according to the method step s could be carried out in combination.

The methods can be carried out serially or in parallel with a statistically significant number of samples under the same conditions—that is, for example, with the same culture medium, with the same bacteria and/or spores in the suspension and/or in the aerosol, with identical incubation conditions, etc.

The method can be carried out at the latest beginning from the sterilization of the device according to method step e under aseptic laboratory conditions on a Cleanbench.

The results of the physical integrity test according to method step b (and/or optionally according to method step m) can be correlated with the results of the BCT tests available after the second incubation phase according to method steps r and/or y.

To evaluate the detection limits of the physical integrity test in correlation with the bacteria challenge test, the process can also be carried out with samples having predetermined defects. The defects in this case can substantially be designed as holes with a diameter of 0.1 to 100 μm.

LIST OF REFERENCE NUMBERS 1, 2, 3 device
4, 5 device
10 medium chamber
11 medium chamber inner chamber
12 lateral wall
15 medium inlet line
15A medium inlet line aseptic connector
15K medium inlet line clamp
15S medium inlet line sterile filter
16 medium outlet line
16K medium outlet line clamp
17 medium sample withdrawal point
19 vent line
19K vent line clamp
19S vent line sterile filter
20 sample holder
40 orienting device
50 suspension chamber
51 suspension chamber inner chamber
52 suspension chamber lateral wall
55 suspension inlet line
55A suspension inlet line aseptic connector
55K suspension inlet line clamp
56 suspension outlet line
56K suspension outlet line clamp
57 suspension sample withdrawal point
59 suspension chamber vent line
59K suspension chamber vent line clamp
59S suspension chamber vent line sterile filter
100 sample

The invention claimed is:

1. A device configured to carry out a bacteria challenge test on a sample (100) of a disposable component, the device comprising:
a sample holder (20) having an outer peripheral region and configured for holding the sample (100) so that opposite first and second surfaces of the sample face in opposite first and second directions;
a medium chamber (10) connected to the outer peripheral region of the sample holder (20) so that the medium chamber (10) and the first surface of the sample (100) form a medium chamber internal space (11), a medium chamber inlet (15) extending into the medium chamber internal space (11) and configured to introduce a liquid culture medium into the medium chamber internal space (11), and a medium chamber vent line (19) extending from a side of the medium chamber (10) opposite the sample holder (20) and being configured to vent the medium chamber internal space (11);
a suspension chamber (50) connected to the outer peripheral region of the sample holder (20) so that the suspension chamber (50) and the second surface of the sample (100) form a suspension chamber internal space (51), a suspension chamber inlet (55) extending into the suspension chamber (50) and configured to introduce a liquid suspension into the suspension chamber internal space (51), and a suspension chamber vent line (59) extending from a side of the suspension chamber (50) opposite the sample holder (20) and being configured to vent the suspension chamber internal space (51); and
an orienting device (40) having a pivot device engaged with the sample holder (20) and passing through a plane of the sample holder (20), the orienting device (40) being configured for rotating the sample holder (20) between a first orientation where the first surface of the sample faces up and the medium chamber vent line (19) is substantially at a highest point of the device and a second orientation where the second surface of the sample faces up and the suspension chamber vent line (59) is substantially at a highest point of the device.

2. The device according to claim 1, wherein at least one transparent region is constructed in a lateral wall (12) of the medium chamber (10).

3. The device according to claim 1, wherein the sample holder (20) is arranged in a detachable connection with the medium chamber (10).

4. The device according to claim 1, wherein the device (1; 2; 3; 4; 5) is designed to be pressure stable under a vacuum of about $1 \times 10^{-10}$ mbar, and up to a pressure of about 2 bar.

5. The device according to claim 1, further comprising at least one electrode for contacting the medium chamber internal space (11) of the medium chamber (10).

6. The device according to claim 1, wherein the medium chamber vent line (19) of the device (1; 2; 3; 4; 5) has a region that is selectively closable.

7. The device according to claim 1, wherein the orienting device (40) further is configured for selectively orienting the medium chamber (10) in an application position such that the sample (100) is oriented with an outer surface inclined to a horizontal frame of reference.

8. The device according to claim 1, wherein the sample holder (20) has a plug element configured for connection with at least one of the medium chamber (10) and the suspension chamber (50).

9. The device according to claim 1, wherein the medium chamber (10) and the suspension chamber (50) have complementary connecting elements for connecting to the sample holder (20).

* * * * *